United States Patent [19]
Sobel et al.

[11] 3,985,823
[45] Oct. 12, 1976

[54] ISOPARAFFIN-OLEFIN ALKYLATION WITH HF ALKYLATION AND ISOMERIZATION IN A SOAKING ZONE

[75] Inventors: Jay E. Sobel, Highland Park; Bipin V. Vora, Wheeling, both of Ill.

[73] Assignee: UOP Inc., Des Plaines, Ill.

[22] Filed: Dec. 22, 1975

[21] Appl. No.: 643,570

Related U.S. Application Data

[63] Continuation-in-part of Ser. No. 426,980, Dec. 20, 1973, abandoned.

[52] U.S. Cl.................. 260/683.42; 260/683.48
[51] Int. Cl.².............................. C07C 3/54
[58] Field of Search........... 260/683.48, 683.45, 260/683.42, 683.68, 683.65

[56] References Cited
UNITED STATES PATENTS

| | | | |
|---|---|---|---|
| 2,376,060 | 5/1945 | Jones............................ | 260/683.68 |
| 2,430,228 | 11/1947 | Kirkpatrick et al............ | 260/683.45 |
| 3,204,011 | 8/1965 | Hettick et al.................. | 260/683.42 |
| 3,408,419 | 10/1968 | Herber et al.................. | 260/683.48 |
| 3,560,587 | 2/1971 | Borst, Jr. ...................... | 260/683.48 |
| 3,607,970 | 9/1971 | Borst, Jr. ...................... | 260/683.48 |
| 3,780,131 | 12/1973 | Sobel............................. | 260/683.45 |
| 3,784,628 | 1/1974 | Chapman...................... | 260/683.42 |
| 3,787,518 | 1/1974 | Anderson...................... | 260/683.45 |

*Primary Examiner*—George Crasanakis
*Attorney, Agent, or Firm*—James R. Hoatson, Jr.; Richard D. Stone; William H. Page, II

[57] ABSTRACT

A process for producing hydrocarbon alkylate from an isoparaffin and an olefin-acting agent. The isoparaffin, the olefin and a first, relatively low strength hydrogen fluoride catalyst are contacted in an alkylation reaction to form a reaction mixture, the reaction mixture is settled to separate a first hydrocarbon phase from the low strength catalyst phase, the first hydrocarbon phase is admixed with a second, relatively higher strength hydrogen fluoride catalyst phase in an alkylation soaker, the effluent from the soaker is settled to separate a second hydrocarbon phase from the high strength catalyst phase, and the hydrocarbon alkylate is recovered from the second hydrocarbon phase.

10 Claims, 1 Drawing Figure

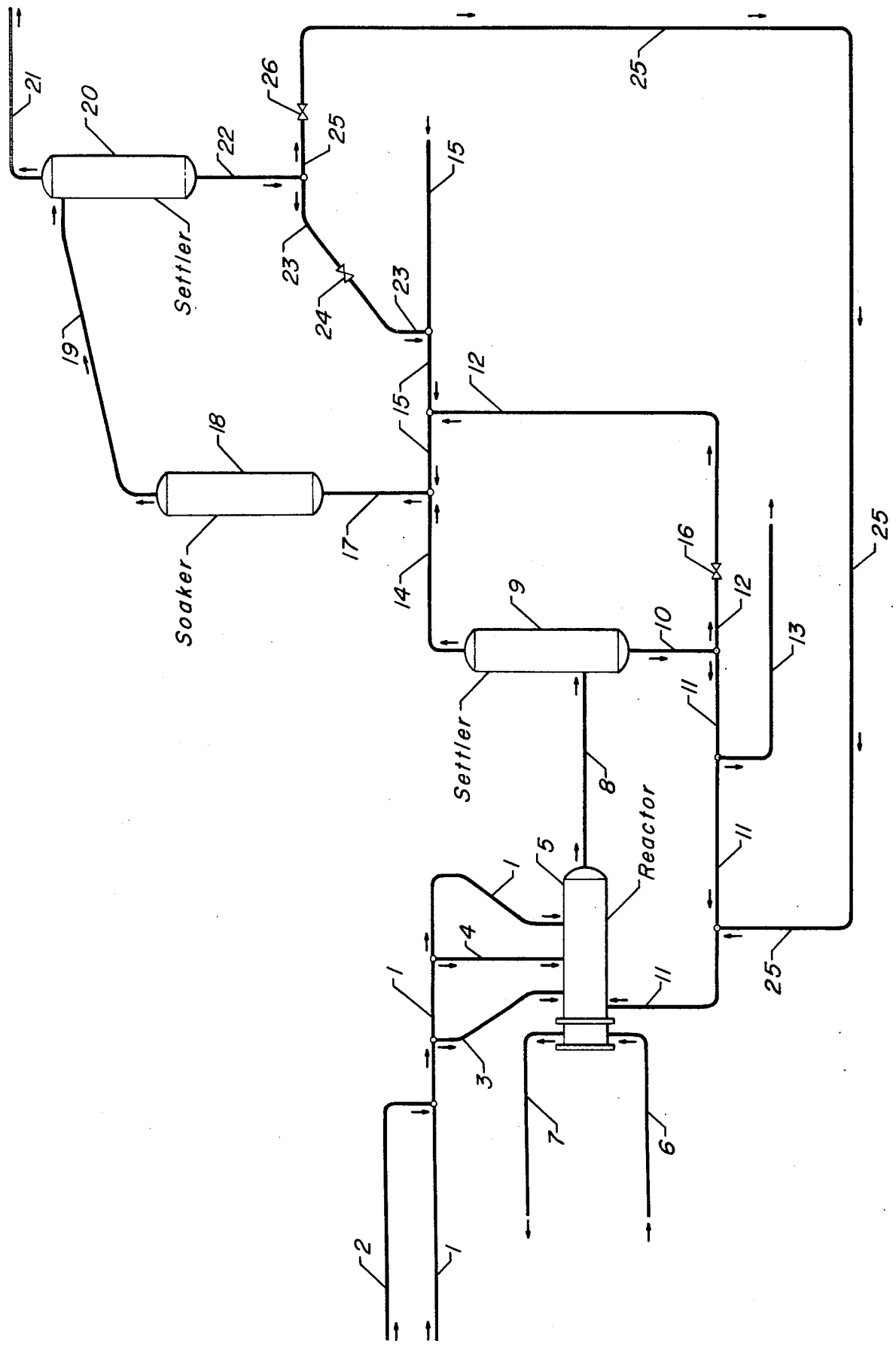

ISOPARAFFIN-OLEFIN ALKYLATION WITH HF ALKYLATION AND ISOMERIZATION IN A SOAKING ZONE

CROSS REFERENCE TO RELATED APPLICATION

This application is a continuation-in-part of our application Ser. No. 426,980, filed Dec. 20, 1973 and now abandoned. The teachings of this application are incorporated by reference.

BACKGROUND OF THE INVENTION

This invention relates to a process for producing an alkylation reaction product from an isoparaffin and an olefin-acting agent, utilizing hydrogen fluoride catalysts. In one aspect, this invention relates to a process for reacting lower molecular weight isoparaffins with lower molecular weight olefins to produce higher molecular weight branched-chain hydrocarbons suitable for use in motor fuel. In another aspect, this invention relates to a method for reducing the alkylation catalyst inventory requirements in a hydrogen fluoride catalyzed alkylation process. In a further aspect, this invention relates to a method for using two hydrogen fluoride catalyst phases, differing in acid strength, in an isoparaffin-olefin alkylation operation.

Alkylation of isoparaffinic hydrocarbons, such as isobutane and isopentane, with olefinic hydrocarbons such as propylene, butylene and amylenes, or with other olefin-acting agents such as $C_3$–$C_5$ alkyl halides, etc., using hydrogen fluoride as a catalyst is well known as a commercially important method for producing gasoline boiling range hydrocarbons. The $C_5$–$C_{10}$ hydrocarbons typically produced in isoparaffin-olefin alkylation operations are termed "alkylate". Alkylate is particularly useful as a motor fuel blending stock. It possesses motor and research octane ratings high enough that it may be employed to improve the overall octane ratings of available gasoline pools to provide motor fuels which comply with the requirements of modern automobile motors. High octane alkylate blending components are particularly important in producing motor fuels of sufficiently high octane when it is desired to avoid use of alkyl lead compounds in the motor fuel. A continuing goal in the art is to provide an economically attractive hydrogen fluoride catalyzed alkylation process which provides an alkylate product having motor and research octane ratings which are higher than are attainable in conventional alkylation processes.

In commercial isoparaffin-olefin alkylation operations using hydrogen fluoride catalyst, generally, isobutane is the isoparaffin used and propylene, butylenes, amylenes, or a mixture of these olefins, are used as the olefin-acting agent. In conventional prior art operations, the isoparaffin, olefin-acting agent and hydrogen fluoride catalyst are first contacted and thoroughly admixed in an alkylation reactor, forming a reaction mixture, or emulsion. After a relatively short time, reaction of the alkylating agent is substantially complete and the reaction mixture is withdrawn from the alkylation reactor and is allowed to settle by gravity into immiscible hydrocarbon and catalyst phases in a settling vessel. The hydrogen fluoride catalyst phase thus separated is returned directly to the alkylation reactor for further catalytic use. The hydrocarbon phase separated in the settling operation is further processed, e.g., by fractionation, to recover the alkylate product and to separate unconsumed isoparaffin for recycle to the alkylation reactor.

It has been found necessary in prior art to maintain conditions in hydrogen fluoride catalyzed isoparaffin-olefin alkylation operations within fairly specific ranges. For example, conditions such as temperature, pressure, reactant and catalyst concentrations, etc., must be carefully regulated in order to provide an acceptable yield of high quality alkylate product. One of the alkylation conditions found to be essential in producing an alkylation reaction product of adequate quality has been the maintenance of a catalyst/hydrocarbon volume ratio above a minimum level in the alkylation reactor. As used herein, the term "catalyst/hydrocarbon volume ratio" means the ratio of the volume of catalyst introduced into a reactor or soaker per unit time divided by the volume of hydrocarbons, including hydrocarbonaceous alkylating agents such as alkyl fluorides, introduced into the reactor or soaker per unit time. It has been found necessary in prior art to maintain a catalyst/hydrocarbon volume ratio in the feeds to an alkylation reactor of at least about 1:1, and a catalyst/hydrocarbon volume ratio of about 1.5:1, or greater, is usually found to provide a product of superior quality. It has been found that, when lower catalyst/hydrocarbon volume ratios are utilized, so that the catalyst/hydrocarbon volume ratio is less than about 1:1 and often even when the catalyst/hydrocarbon volume ratio is less than 1.5:1, that the olefin concentration in the catalyst becomes relatively high, and results in a high rate of olefin polymerization in the alkylation reactor. It is well known in the art that olefin polymerization is a very undesirable side reaction, using up large amounts of valuable olefin feedstocks and producing low octane, overly high boiling product hydrocarbon. Efforst are normally made to avoid olefin polymerization in the alkylation reactor, if possible. Thus, it has been found essential in prior art to maintain the catalyst/hydrocarbon ratio in the alkylation reactor at a relatively high level, generally about 1:1 or more, in order to provide a high quality alkylate product and to avoid excessive consumption of olefinic feedstocks.

Another of the alkylation conditions found conducive to the production of high quality alkylate product in commercial operations has been the use in the alkylation reactor of a hydrogen fluoride alkylation catalyst having a relatively low acid strength (e.g., less than about 95 weight percent hydrogen fluoride and preferably between about 80 weight percent and about 90 weight percent hydrogen fluoride). Higher strength hydrogen fluoride alkylation catalyst may be used; however, the quality of the alkylate product produced using higher strength catalyst is significantly less than the quality of alkylate produced when lower strength catalyst, having the preferred 80–90 weight percent acid strength, is used in the alkylation reactor.

In a relatively recent modification, a reaction soaker has been added to the conventional alkylation scheme. The hydrocarbon reactants and hydrogen fluoride catalysts are first charged to a reactor-cooler equipped with heat exchange means and the reactants and catalyst are thoroughly admixed therein to form a reaction mixture. Within a short period of residence time, e.g., about 0.1–2 minutes, substantially all of the olefins charged to the reactor-cooler react with isoparaffin to form alkylate hydrocarbons with the simultaneous formation of large amounts of heat energy. This heat energy is removed from the reaction mixture in the reactor-cooler in order to maintain the reaction mixture at a fairly uniform temperature. After a short 0.1–2 minute residence time in the reactor-cooler, rather than simply settling the reaction mixture as in prior art, the reaction mixture is passed from the reactor into the reaction soaker which generally does not have heat exchange means. The reaction soaker is typically a relatively large vessel equipped with perforated trays, baffle sections or other means for maintaining the immiscible hydrocarbons and catalyst in the reaction mixture in the form of an emulsion. The reaction mixture is retained in the reaction soaker for a relatively long residence time, e.g., about 2–60 minutes. The reaction mixture is then removed from the reaction soaker and passed to a conventional settler for gravity separation into hydrocarbon and catalyst phases. It has been found that the use of a reaction soaker as described results in a substantial improvement in the quality and purity of the alkylate product in comparison with alkylation operations which employ only a conventional reactor or reactor-cooler. Use of the soaker has been found to provide a substantial increase in the motor and research octane ratings of the alkylate produced. This is believed to be due primarily to isomerization of relatively low octane alkylate hydrocarbons, such as dimethylhexane, within the soaker to form additional quantities of relatively high octane alkylate hydrocarbons, such as trimethylpentanes. Use of the reaction soaker has also been found to result in a reduction in the concentration of undesirable alkyl fluorides in the hydrocarbons treated in the reaction soaker, substantially eliminating the problem of fluoride contamination of the alkylate product.

Although use of the alkylation soaker as described above provides a substantial overall improvement relative to conventional alkylation operations, the long residence time of the reaction mixture within the soaker necessitates the use of a very large total inventory of hydrogen fluoride catalysts in the overall alkylation operation, with the major portion of the total inventory of catalyst in the overall system being located within the soaker at any given time. The relatively large amount of catalyst thus needed in the overall operation necessitates the use of larger size equipment in several sections of the alkylation system. The increased cost of maintaining this large catalyst inventory partially offsets the advantages obtained by using the reaction soaker. For example, every commercial alkylation operation generally includes a large catalyst storage drum which is of sufficient size to contain all of the catalyst used in the overall system when necessary. The catalyst inventory is stored in the drum during periods when the overall operation is shut down for any reason. When the catalyst inventory needed in an alkylation operation is substantially increased by the use of an alkylation soaker, the size of the catalyst storage drum must also be increased substantially. Further, the relief valve for catalyst storage drum and relief gas neutralization equipment must also be enlarged along with the catalyst storage drum. Heretofore, the beneficial results obtained using a reaction soaker in an alkylation operation have been, to some extent, hindered by the larger catalyst inventory thus required and the attendant increased investment and operating costs associated with the use of the soaker.

Other researchers have also been concerned with the problems caused by operating an HF alkylation zone with relatively low strength HF acid. Some researchers have thought that the problem was removal of alkyl fluorides from an alkylate. The solution proposed was to contact the alkylate in a contacting zone with HF acid of high purity. See U.S. Pat. Nos. 3,763,264 (Class 260 683.42) and 3,784,628 (Class 260–683.42), the teachings of which are incorporated by reference. In these patents, the patentee contacts the alkylate, containing alkyl fluorides, in a special contacting zone wherein the alkylate contacts high purity HF acid. In one patent, the HF acid is indicated as coming from the overhead of the HF acid rerun column and a separate HF fraction from the depropanizer column, in U.S. Pat. No. 3,763,264. Both of these HF acid sources would be relatively high purity, and both would be substantially free of any organic diluent, or acid soluble oil. In U.S. Pat. No. 3,784,628, the HF acid used is 98 wt. % pure, though the specific source of this acid is not mentioned.

In both of these mentioned patents, the patentee is concerned with removal of alkyl fluorides. If a refiner is only interested in removing alkyl fluorides, the very high acid purities suggested in these patents would be optimum. High acid strengths promote break down of alkyl fluorides into olefins and HF acid. Unfortunately, the patentees do not seem to appreciate the fate to be suffered by the olefins will very quickly react in these contacting zones, and the alkylate formed therefrom will be of a relatively low quality. The alkylate will be of low quality because the HF acid used does not contain any organic diluent or acid soluble oil, to attenuate the activity of the HF acid catalyst. The net effect of such an operation will be to increase slightly the end point of the gasoline, and slightly lower the octane number of the alkylate.

The process of this invention helps eliminate such problems and may be used to provide an alkylation operation having a substantially reduced catalyst inventory requirement while the high quality product obtained by employing a soaker is further improved.

Although better quality alkylate is produced when relatively low strength (80–90 weight percent) hydrogen fluoride catalyst is employed in the alkylation reactor, it has been found that improved results are obtained when a higher strength (e.g., greater than 90 weight percent, and preferably 90 to 95 weight percent) hydrogen fluoride catalyst is employed in an alkylation soaker. Thus, in an optimum system, lower strength hydrogen fluoride catalyst would be utilized in the alkylation reactor while higher strength hydrogen fluoride catalyst containing organic diluent would be utilized in the soaker. Heretofore, use of two distinct hydrogen fluoride catalyst phases, differing in acid strength, in an alkylation operation employing an alkylation soaker has not been possible, since the reaction mixture of hydrogen fluoride catalyst and hydrocarbons has been passed directly from the alkylation reactor-cooler into the soaker, the same hydrogen fluoride catalyst phase being used both is the reactor-cooler and the soaker. The process of the present invention provides an economical and convenient method for employing two hydrogen fluoride catalyst phases, differing in acid strength, in an alkylation operation using a soaker, while avoiding product degradation which would occur if an organic diluent free acid was used in a soaker.

SUMMARY OF THE INVENTION

Accordingly, the present invention provides a process for producing an alkylation reaction product from an isoparaffin and an olefin, which comprises the steps of: (a) reacting said olefin with said isoparaffin in admixture with a relatively low strength hydrogen fluoride catalyst containing 75 to 95 wt. percent HF at a catalyst to hydrocarbon ratio of 1:1 to 5:1; (b) settling the resultant reaction mixture to separate the same into a hydrocarbon phase and a catalyst phase; (c) commingling with said hydrocarbon phase, without further addition of olefin, a relatively high strength catalyst of hydrogen fluoride and organic diluent containing 90 to 98 wt. percent HF, and more HF than contained in said relatively low strength catalyst in a lower catalyst to a hydrocarbon volume ratio than step (a); (d) introducing the resulting mixture into a soaking zone and therein isomerizing lower octane alkylate hydrocarbons to higher octane alkylate hydrocarbons, converting alkyl fluorides into high quality alkylate and HF acid, by maintaining the last mentioned mixture in the soaking zone at a temperature of 50 to 120 F for 5 to 20 minutes; (e) separating the effluent of the soaking zone into a second hydrocarbon and a second catalyst phase, and; (f) recovering said alkylation reaction product from said second hydrocarbon phase.

The present invention provides a particularly advantageous method for utilizing in an alkylation operation two hydrogen fluoride catalysts of different acid concentrations, in order to provide optimum conditions for the production of high-quality alkylate, not only with respect to an alkylation reactor, but also with respect to an alkylation soaker. In addition, by employing a relatively low catalyst/hydrocarbon volume ratio in the feed to the alkylation soaker in addition to employing the desirable high strength catalyst, catalyst inventory requirements may be reduced substantially by using the present process with a simultaneous improvement in the quality of the alkylate produce produced.

Further objects, embodiments and advantages of the process of the present invention will be apparent to those skilled in the art from the following description of the attached drawing and detailed description of the invention.

DESCRIPTION OF THE DRAWING

The attached drawing is a schematic illustration of one embodiment of the process of the present invention. In the embodiment illustrated, the isoparaffin utilized is isobutane and the olefin-acting agent utilized comprises a mixture of propylene and butylenes. The scope of the present invention is not limited to the embodiment thus depicted. Various other suitable reactants and embodiments will be apparent to those skilled in the art from the description hereinafter provided.

Referring to the drawing, conventional isobutane alakylation feedstock, comprising about 95 weight percent isobutane, is introduced into the operation via conduit 1. Conventional olefinic alkylation feedstock, comprising propylene and butylenes, is introduced into the process by conduit 2 and charged into admixture with the isobutane feed in conduit 1. The resulting hydrocarbon reactor charge stream is passed further through conduit 1 and through conduits 3 and 4 into alkylation reactor-cooler 5. Multiple conduits are employed for charging the hydrocarbon reactor charge into reactor-cooler 5 in order to effect efficient mixing of the reactant hydrocarbons with hydrogen fluoride alkylation catalyst and to prevent generation of undesirably large amounts of heat in any particular section of reactor-cooler 5. Conventional hydrogen fluoride alkylation catalyst, comprising about 85 weight percent hydrogen fluoride, is charged into reactor-cooler 5 via conduit 11. The hydrocarbons and catalyst are throughly admixed in reactor-cooler 5 to form a reaction mixture, or emulsion. Substantially all of the olefins charged to reactor-cooler 5 undergo the alkylation reaction with isobutane in a relatively short time, with the simultaneous release of the heat of reaction. In order to remove the heat of reaction, cooling water is passed into reactor-cooler 5 via conduit 6 and is passed indirect heat exchange with the reaction mixture using heat exchange means not shown. Used cooling water is withdrawn from reactor-cooler 5 via conduit 7. Alkylation conditions maintained in reactor-cooler 5 include a temperature of about 90°F., a pressure sufficient to maintain liquid phase operations, and a contact time of about 1 minute. Hydrocarbons and catalyst are charged to reactor-cooler 5 at relative rates sufficient to provide a catalyst/hydrocarbon volume ratio of about 1.5:1 in the reaction mixture in reactor-cooler 5. Reaction mixture which is substantially free from unreacted olefins, and which contains primarily isobutane, alkylate and hydrogen fluoride catalyst, is withdrawn from reactor-cooler 5 via conduit 8 and passed into settler 9. The reaction mixture is allowed to stand without agitation in settler 9, allowing the hydrogen fluoride catalyst to form a heavier phase and the hydrocarbon components of the reaction mixture to form a lighter phase. The catalyst phase is withdrawn from the bottom of settler 9 via conduit 10. Catalyst from conduit 10 is preferably passed into the higher strength catalyst phase used in the soaker-settler system described hereinafter. In such cases, valve 16 is opened sufficiently to allow the desired amount of lower strength catalyst to flow from conduit 10 through conduit 12. The low strength acid from conduit 10 is a convenient source or organic diluent to attenuate the activity of higher strength acid in the soaker-settler.

In commercial alkylation operations, it is necessary to treat, continuously or intermittently, a portion of the used alkylation catalyst for removal from the catalyst of excessive amounts of non-acid catalyst components and impurities (such as water and hydrogen fluoride-soluble organic compounds) in order to maintain the desired acid strength in the catalyst. Such regeneration of hydrogen fluoride alkylation catalyst is conventional, and its practice well known to those skilled in the art. In the embodiment of this invention illustrated in the drawing, regeneration is accomplished by withdrawing a small slip stream of catalyst from conduit 11 by way of conduit 13 and passing the catalyst stream in conduit 13 to conventional regeneration means not shown. The primary portion of the catalyst stream in conduit 11 is recycled to reactor-cooler 5 for catalytic use as described above. Regenerated, high strength catalyst which is recovered from the regeneration operation, is passed back into the system as described hereinafter in order to upgrade the strength of the hydrogen fluoride catalysts used. Referring again to settler 9, the lighter hydrocarbon phase therein is withdrawn via conduit 14. High strength hydrogen fluoride catalyst, comprising about 95 weight percent hydrogen fluoride, from conduit 15 and the hydrocarbon stream from conduit 14 are admixed in conduit 17 and charged to soaker 18. The admixed hydrocarbons and high strength catalyst are charged to soaker 18 at a catalyst/hydrocarbon volume ratio of about 0.1. Soaker 18 contains several perforated trays which serve to maintain the high strength catalyst and hydrocarbons charged to soaker 18 in an emulsified or dispersed state of admixture. The temperature and pressure maintained in soaker 18 are approximately the same as the temperature and pressure employed in reactor-cooler 5. After a contact time of about 10 minutes in soaker 18, the admixed hydrocarbons and high strength catalyst are withdrawn via conduit 19 and passed into settler 20. In settler 20 the admixed high strength catalyst and hydrocarbons are settled in the conventional manner into separate catalyst and hydrocarbon phases. The lighter hydrocarbon phase is withdrawn from settler 20 via conduit 21 and is then passed to further conventional fractionation and product separate operations not shown. The heavier, high strength catalyst phase is withdrawn from the bottom of settler 20 via conduit 22. A relatively small portion of the higher strength catalyst stream in conduit 22 is passed into conduit 25 in normal, steady state operations, while the major portion is passed into conduit 23. In such normal, steady state operation of the system, sufficient high strength catalyst is passed through conduit 25 and combined with the lower strength hydrogen fluoride alkylation catalyst in conduit 11 to replace catalyst and dissolved hydrogen fluoride which are removed or lost from the lower strength catalyst which is circulating between reactor-cooler 5 and settler 9. For example, some of the lower strength catalyst is removed from conduit 11 via conduit 13 and passed to regeneration, as described above. Further amounts of hydrogen fluoride are lost from the lower strength catalyst system as a solution in the hydrocarbon phase removed from settler 9 via conduit 14. Thus, the high strength catalyst charged to conduit 11 through conduit 25 is utilized both to maintain the lower strength alkylation catalyst at the desired acid strength and also to replace any hydrogen fluoride which is removed from the lower strength alkylation catalyst circulation system. Referring again to the higher strength catalyst system, substantially pure hydrogen fluoride is introduced into the system by way of conduit 15. The substantially pure hydrogen fluoride charged into conduit 15 may be freshly introduced but preferably is provided from the conventional regeneration operation and from hydrogen fluoride recovered from conventional fractionation and product purification schemes in the alkylation system. The major portion of the high strength catalyst phase which is removed from settler 20 via conduit 22, is passed through conduit 23 and commingled with the freshly introduced, substantially pure hydrogen fluoride in conduit 15. The high strength catalyst in conduit 15 is passed further into admixture with hydrocarbons in conduit 17 as described above. A relatively small portion of the catalyst stream circulating through conduits 10 and 11 is charged via conduit 12 into conduit 15. If organic diluent is added to the acid in the soaker-settler from an outside source, e.g., the bottoms fraction of the HF acid regenerator, then valve 16 in line 12 may be closed.

In cases where little or no hydrogen fluoride is being removed from the lower strength catalyst phase circulating between reactor-cooler 5 and settler 9, valve 26 may be shut off completely for some time, and thus all the high strength catalyst will be charged through conduit 23 and conduit 15 back into soaker 18. Some conventional equipment and steps which are required for the operation of the embodiment described in the foregoing have been omitted from the drawing and the description thereof. For example, certain pumps, valves, etc., may be needed in order to operate the described embodiment. The use and placement of such conventional items will be obvious to those skilled in the art.

DETAILED DESCRIPTION OF THE INVENTION

The alkylation process of the present invention may be applied, in general, to the alkylation of isoparaffins, particularly $C_4$–$C_6$ isoparrafins. The preferred isoparaffins are isobutane and isopentane, particularly isobutane. A mixture of two or more isoparaffins may also be employed, if desired. A suitable isoparaffin feedstock for use in the present process may contain some nonreactive contaminants such as normal paraffins. For example, a conventional commercial isobutane alkylation feedstock generally contains about 95 weight percent isobutane, 4 weight percent normal butane and 1 weight percent propane. It is well known in the art that the isoparaffin employed in an alkylation system is generally recycled and thus may contain substantial amounts of contaminants built up by recycle to concentrations in excess of a fresh feedstock.

Olefin-acting compounds which are suitable for use in the process of the present invention include $C_3$–$C_6$ mono-olefins, alkyl halides, or mixtures thereof. $C_3$–$C_5$ olefins are preferred. The process of the present invention may be applied to the alkylation of mixtures of two or more olefin-acting compounds with the same benefits and improvements as would be obtained in using a single olefin-acting compound. For example, many conventional olefin feedstocks utilized in commercial alkylation operations contain mixtures of propylene and butylenes, or propylene, butylenes and amylenes. Application of the present process to such olefin mixtures results in improvements in quality of the products obtained which are equal to the improvements obtained using a single olefin. Similarly, a mixture of $C_3$–$C_5$ alkyl halides and olefins in any proportion is also suitable in many cases, for example, when the halide is fluoride. The particularly preferred $C_3$–$C_5$ olefin feedstocks are conventionally derived from petroleum refining processes such as catalytic cracking and may contain substantial amounts of saturates, lighter and heavier olefins, etc. Olefin feedstocks derived from such conventional sources are suitable for use in providing the olefin-acting agent used in the present process.

The low strength hydrogen fluoride catalyst employed in the present process to react the isoparaffin and the alkylating agent in the alkylation reactor may suitably be any conventional hydrogen fluoride catalyst used in isoparaffin-olefin alkylation operations in prior art. Such conventional hydrogen fluoride catalysts contain from about 75 to about 95 weight percent of titratable acid; however, a titratable acid content of between about 80 and about 90 weight percent in the alkylation catalyst has been found to give best results. Such conventional hydrogen fluoride catalysts contain less than about 5 weight percent water, with less than about 1 weight percent water being preferred. The remainder of the conventional catalyst is made up of hydrogen fluoride-soluble organic diluent compounds. In prior art, the titratable acid strength in hydrogen fluoride alkylation catalysts has been maintained at the desired level by continuously or intermittently withdrawing a small amount of the catalyst from circulation in the reactor-settler system and passing the withdrawn portion of catalyst regeneration system. In conventional catalyst regeneration system relatively pure hydrogen fluoride is separated from a constant boiling mixture of water and hydrogen fluoride and from heavy, hydrogen fluoride-soluble organic compounds such as polymers and organic fluorides. The relatively pure hydrogen fluoride produced by conventional regeneration has, in prior art, been passed directly back into the primary catalyst phase which is in circulation in the reactor-settler system. By adding a controlled amount of pure hydrogen fluoride to the circulating catalyst and simultaneously withdrawing a controlled amount of the diluted catalyst, titratable acid strength in the catalyst has been maintained by compensating for dilution and contamination of the catalyst. Catalyst contamination and dilution are caused at least in part by water in the hydrocarbon reactant feedstock, polymer formation in the alkylation reactor, etc., which cause buildup of diluents and contaminants in the circulating catalyst at a slow but relatively constant rate.

The amount of high strength catalyst required to be admixed with the lower strength catalyst to maintain the desired material balance and acid strength in the lower strength catalyst phase will vary according to the respective strengths of the two catalyst phases, the rate of dilution of the lower strength catalyst phase, etc., and will be obvious to those skilled in the alkylation art.

A large number of alkylation reactors suitable for use in the process of this invention are known in the art. For example, but not by way of limitation, the alkylation reactor-coolers described in U.S. Pat. No. 3,456,033, U.S. Pat. No. 3,469,949 and U.S. Pat. No. 3,501,536, the teachings of which are incorporated by reference, may suitably be employed in the present process. Particular alkylation conditions necessarily associated with the use of a particular alkylation reactor, or reactor-cooler, such as those described in the above-listed patents or in connection with other suitable conventional alkylation reactors, are also well known and may be used in embodiments of the present invention in connection with the detailed description of the alkylation conditions utilized in a reactor-cooler which are provided hereinafter.

Alkylation conditions employed in the reactor-cooler in the present process include a temperature of about 1°F. to about 200°F., a pressure sufficient to maintain the reactants, catalyst and reaction product in the liquid phase, a catalyst/hydrocarbon volume ratio of about 1:1 to about 5:1 or more, and isoparaffin/olefin mole ratio of about 6:1 to about 30:1 and a contact time of about 0.1 minutes to about 5 minutes. When the preferred reactants, isobutane and $C_3-C_5$ olefins are employed, preferred alkylation conditions include a temperature of about 50°F. to about 125°F., a catalyst/hydrocarbon volume ratio of about 1.5:1 to about 2.5:1 and a contact time of about 0.2 minutes to about 2 minutes. The hydrogen fluoride alkylation catalyst is generally immiscible with the isoparaffin reactant and with the alkylation reaction products formed in the alkylation reactor, so that various means for mixing or agitation of the lower strength catalyst phase and the hydrocarbons are generally employed in the alkylation reactor in order to provide the reaction mixture, or emulsion, of catalyst and immiscible hydrocarbons. Some heat removal means is generally necessary for satisfactory operation of the alkylation reactor. Various means for accomplishing heat withdrawal and temperature control in the alkylation reactor are known in the art, any of which may suitably be employed in the present process. For example, in a preferred embodiment heat generated as heat of reaction in the alkylation reactor may be removed from the reaction mixture by use of a combination reactor-cooler, which includes indirect heat exchange between a cooling fluid and the reaction mixture within the reactor-cooler. Precooling of the hydrocarbon reactants or hydrogen fluoride alkylation catalyst has also been utilized in order to maintain the desired temperature in the reactor-cooler.

A variety of vessels which are suitable for use in settling the reaction mixture to separate a hydrocarbon phase from the lower strength catalyst phase are well known in the alkylation art. The effluent from the alkylation reactor is conventionally settled to separate hydrocarbon phase from the alkylation catalyst. The hydrocarbon phase contains the alkylation reaction product and excess isoparaffin. The hydrocarbons and catalyst are maintained at about the same temperature and pressure in the settling operation as are used in the alkylation reactor. In prior art alkylation operations utilizing a soaker, the reaction mixture has been passed directly from the alkylation reactor into the soaker. The reaction mixture removed from the soaker has then been charged to a conventional settler for complete separation of the catalyst and hydrocarbon phases. In the present process, in contrast, the hydrocarbon effluent from the alkylation reactor is completely separated from the lower strength catalyst phase by settling. The lower strength catalyst phase is then recycled directly to the alkylation reactor, while the resulting hydrocarbon phase is passed to the alkylation soaker where it is admixed with the higher strength hydrogen fluoride catalyst described hereinafter.

The hydrocarbon phase recovered from the first settling operation in the present process is admixed with a hydrogen fluoride catalyst phase containing from about 90 weight percent to about 98 weight percent titratable acid in an alkylation soaker. The hydrogen fluoride catalyst phase employed in the soaker preferably contains about 95 weight percent titratable acid, or more, and in any case it is essential to the present process that the catalyst phase employed in the soaker contain a higher titratable acid content than the acid strength in the lower strength catalyst phase which is utilized in the alkylation reactor. The relatively high acid content of the high strength hydrogen fluoride catalyst phase used in the soaker is preferably provided during normal operation of the process by charging substantially pure hydrogen fluoride from various conventional sources into the high strength catalyst phase, as needed to maintain high acid strength. For example, substantially pure hydrogen fluoride may be obtained as fresh acid from a source outside the alkylation operation, as well as from conventional catalyst regeneration systems which form a normal part of alkylation operations. Substantially pure hydrogen fluoride may also be recovered as a separate phase which settles out in various receiving vessels, settlers, etc., in the conventional fractionation and purification equipment used in alkylation operations. Such sources of substantially pure hydrogen fluoride are well known to those skilled in the alkylation art. By employing the high strength hydrogen fluoride catalyst phase in the alkylation soaker, the beneficial effects on the quality of the alkylate product which are obtained when a soaker is employed are actually improved over conventional use of a soaker.

It is also essential to the practice of the present invention that the higher strength acid contain sufficient organic diluent to attenuate the high activity of pure HF acid. The acid must contain 2 to 10, and preferably about 5 wt. percent organic diluent from optimum operation of the soaker-settler. The high strength catalyst is particularly effective in producing the desired isomerization of lower octane alkylate hydrocarbons to provide higher octane produces. The high strength catalyst is also highly effective in eliminating undesirable alkyl fluorides which may be present in the alkylate containing hydrocarbons. Such alkyl fluorides are otherwise difficult to separate from the alkylate produce, since they often have a boiling range similar to that of the alkylate. By maintaining a distance and separate catalytic phase of high strength hydrogen fluoride catalyst and by using conventional sources of relatively pure hydrogen fluoride and conventional organic diluents to provide such a high strength catalyst phase, the present process provides a convenient and economical method for utilizing the high strength catalyst obtainable in an alkylation operation.

Although not essential to the operation of the present process, the use of a separate high strength catalyst phase in the soaker is particularly advantageous when it is desired to use a low catalyst/hydrocarbon volume ratio in the alkylation soaker in order to reduce catalyst inventory requirements in the overall alkylation operation. As discussed above, high strength catalyst is more effective in the alkylation soaker than is conventional low acid strength catalyst; however, the low acid strength catalyst provides superior results when used as an alkylation catalyst. Using prior art alkylation methods, it has not been possible to employ more than one catalyst phase in the overall alkylation operation, so that maximum efficiency in both the alkylation reactor and the alkylation soaker could not thereby be obtained. By employing the present process, best use can be made of both the alkylation reactor and the soaker. For example, optimum use of the alkylation reactor requires a relatively large amount of lower strength hydrogen fluoride catalyst, while a relatively small amount of higher strength hydrogen fluoride catalyst is preferable in the soaker. By utilizing the high strength catalyst phase at a relatively low catalyst/hydrocarbon volume ratio in the soaker, the present process can be utilized to avoid the very large overall catalyst inventories which have characterized prior art use of alkylation soakers. The use of high strength acid, attenuated with organic diluent, in the soaker-settler also avoids the formation of undesirable, high end point alkylate which occurs in prior art methods using an organic diluent free HF acid to contact alkyl fluorides. Further, the high strength acid of the present invention will promote isomerization of alkylate, as the acid contains organic diluent. A pure HF acid catalyst does not act as a satisfactory isomerization catalyst is this service. At the same time, alkylate quality is improved through the use of higher strength catalyst, so that the low catalyst/hydrocarbon volume ratio employed in the soaker results in no adverse effects on alkylate quality.

In the present process, after the hydrocarbon phase has been separated from the lower strength alkylation catalyst, the hydrocarbon phase and the higher strength hydrogen fluoride catalyst are charged to the soaker at a catalyst/hydrocarbon volume ratio between about 0.01 and about 5:1. Preferably the catalyst/hydrocarbon volume ratio of the catalyst-hydrocarbon mixture passed into the soaker is maintained within the range from about 0.01:1 to about 1:1, and particularly preferred range of operation in the present process includes a catalyst/hydrocarbon volume ratio between about 0.05:1 and about 0.15:1.

The settled, lower strength catalyst phase is preferably recycled from the first settler directly back to the alkylation reactor. Since only a small amount of the lower strength hydrogen fluoride catalyst used in the alkylation reactor in the present process is employed in the soaker, to supply organic diluent to the higher strength acid therein, a very significant reduction in overall catalyst inventory requirements may be obtained when the preferred, low catalyst/hydrocarbon volume ratio is employed in the alkylation soaker. The benefits obtained by employing the soaker in the alkylation operation of the present process are fully obtained by passing the catalyst-hydrocarbon mixture into the soaker at a low catalyst-hydrocarbon volume ratio, and the operation of the soaker is improved by the use of the high strength catalyst phase in the soaker. By using the preferred, low catalyst/hydrocarbon volume ratio in the soaker alone, and not in the alkylation reactor, the required high catalyst/hydrocarbon volume ratio may be maintained in the alkylation reactor in order to prevent a high degree of olefin polymerization in the reactor, while simultaneously the benefits of the soaker are improved and the drawbacks of prior art use of alkylation soakers are obviated.

The soaking zone employed in the present process may be any suitable alkylation soaker or any other suitable vessel known to those skilled in the art. For example, the soakers shown and described in U.S. Pat. Nos. 3,560,587 and 3,607,970 may suitably be employed in the present process. A variety of other vessels which may suitably be employed as an alkylation soaker in the present process will also be obvious to those skilled in the art. Conventional alkylation soakers are typically vessels equipped with perforated trays, baffle sections or the like in order to maintain the admixed high strength catalyst and hydrocarbons which are charged thereto in the form of a fairly homogenous mixture or emulsion for the desired contact time in the soaker.

Soaking conditions in the present process in addition to the catalyst/hydrocarbon volume ratio discussed above, also include a temperature of about 50° to about 120°F., a pressure sufficient to maintain the catalyst and hydrocarbon charged to the soaker in the liquid phase, and a contact time of about 2 minutes to about 60 minutes in the soaker. Preferably, a contact time between the high strength catalyst and hydrocarbons in the soaker of about 5 minutes to about 20 minutes is employed.

The mixture of catalyst and hydrocarbon removed from the soaking zone after the desired residence time is passed to a conventional settler, wherein the soaker effluent is settled in the conventional manner to separate the high strength catalyst from the hydrocarbon phase. The settled hydrocarbon phase recovered from the second settler is passed to further conventional separation operations, such as fractionation, in order to recover the alkylate product and to separate excess isoparaffins for further conventional recycle to the alkylation reactor.

The high strength catalyst phase recovered by settling the effluent from the soaker is generally recycled to the soaker for further use as described above. A portion of the high strength catalyst phase may be admixed with the lower strength catalyst phase used in the alkylation reactor so as to maintain the desired acid strength in the lower strength catalyst phase and also to provide a sufficient makeup of lower strength catalyst to offset any losses of the lower strength catalyst to e.g., regeneration, solution in settled hydrocarbons, etc. In a preferred embodiment of the present process, controlled amounts of the lower strength catalyst phase are mixed with the higher strength catalyst phase in order to provide the necessary volume of higher strength catalyst. However, it is essential to maintain the lower strength catalyst phase essentially separate from the higher strength catalyst phase during normal operations in order to maintain the two distinct catalyst phases at differing titratable acid strengths.

The alkylation reaction product produced in the present process when the preferred isobutane and $C_3$ and $C_4$ olefins reactants are employed, include $C_7$ and $C_8$ saturated hydrocarbons resulting from the alkylation reaction of the isobutane with the olefins. The primary reaction products include, for example, dimethylhexanes and trimethylpentanes. It is well known in the art that more highly branched hydrocarbons possess superior properties as motor fuel components, and the present invention is directed, in part, to providing an alkylation reaction product containing a higher ratio of more highly branched hydrocarbons, such as trimethylpentanes, to less branched hydrocarbons, such as dimethylehexanes. The foregoing is accomplished through the use of the combination of the alkylation reactor and the alkylation soaker with the use of two separate hydrogen fluoride catalyst phases differing in titratable acid strength. Thus, optimum alkylation conditions are maintained both in the alkylation reactor and in the soaker. In addition, use of the higher strength hydrogen fluoride catalyst in the alkylation soaker results in improved operation of the soaker when the catalyst/hydrocarbon volume ratio used in the soaker is maintained even at a very low level. Use of the low catalyst/hydrocarbon volume ratio, in turn, results in a substantial reduction in the overall catalyst requirements of the alkylation process in contrast to prior art alkylation operations employing a soaker. It is thus apparent that the present invention provides a process for producing superior motor fuel alkylate products by a method more economical and convenient than has been available in the prior art.

ILLUSTRATIVE EMBODIMENT

In order to illustrate one preferred mode of operation of the process of the present invention, a system identical to that shown in the attached drawing is employed. Conventional fresh and recycle isobutane alkylation feed and conventional fresh butylenes alkylation feed are passed into the system through conduits 1 and 2 at the rate of 46,000 barrels per day and at an isobutane/butylene mole ratio of about 10:1. The hydrocarbon reactor charge stream thus formed is passed through conduits 1, 3 and 4 into reactor 5. Low strength (slightly greater than 85 weight percent tetratable acid) hydrogen fluoride alkylation catalyst is passed into reactor 5 by way of conduit 11 at the rate of 67,000 barrels per day. The catalyst and hydrocarbons charged into reactor 5 are contacted and admixed therein for a contact time of 0.5 minutes at a temperature of 90°F. and a pressure sufficient to maintain the hydrocarbons and catalyst as liquids. The reaction mixture of catalyst and hydrocarbons formed in reactor 5, subsequent to the reaction of substantially all the olefins charged to the reactor, is withdrawn from reactor 5 and passed through conduit 8 into settler 9. This latter step is in contrast to prior art alkylation operation utilizing a soaker, wherein reaction mixture withdrawn from the alkylation reactor is passed directly to a soaker. In the present process, reaction mixture is continuously settled in settler 9 to separate the lower strength catalyst from a hydrocarbon phase. Settled, lower strength catalyst is withdrawn from settler 9 at a rate of 67,050 barrels per day, and passed through conduit 10 into conduit 11. Valve 16 passes 375 barrels per day of lower strength catalyst to the soaker-settler via line 12. A slip stream of lower strength catalyst is withdrawn from conduit 11 by way of conduit 13 at the rate of 350 barrels per day, and is passed to catalyst regeneration means not shown. A settled hydrocarbon phase, containing primarily isobutane, hydrocarbon alkylate and some dissolved hydrogen fluoride, is withdrawn from settler 9, via conduit 14 at the rate of 40,000 barrels per day isobutane, 5,000 barrels per day alkylate hydrocarbons and 450 barrels per day dissolved hydrogen fluoride. The hydrocarbon stream in conduit 14 is passed into conduit 17 and admixed therein with (about 95 weight percent hydrogen fluoride) hydrogen fluoride from conduit 15 which is passed into conduit 17 at the rate of about 4,050 barrels per day. The mixture of hydrocarbons and high strength hydrogen fluoride is passed from conduit 17 into soaker 18. In soaker 18, the admixed high strength catalyst and hydrocarbons are maintained in intimate contact for a contact time of about 10 minutes at a temperature of about 90°F. and a pressure sufficient to maintain the hydrocarbons and catalyst as liquids. Using the present process, a substantially smaller amount of hydrogen fluoride may be used in a soaker than has heretofore been possible in prior art alkylation operations including a soaker. Use of high strength catalyst in soaker 18 provides optimum results in the soaker, while the relatively high (1.5:1) catalyst/hydrocarbon volume ratio utilized in reactor 5 need not also be used in soaker 18, as has been necessary in prior art. The admixture of high strength hydrogen fluoride catalyst and hydrocarbons is removed from soaker 18 after about 10 minutes contact time and passed through conduit 19 into settler 20. In settler 20, a high strength, about 95 wt percent hydrogen fluoride phase is separated from a hydrocarbon phase. The hydrocarbon phase separated in settler 20 is removed via conduit 21 and passed, at the rate of 40,000 barrels per day isobutane, 5,000 barrels per day alkylate hydrocarbons and 450 barrels per day dissolved hydrogen fluoride, to conventional fractionation and purification operations for recovery of the alkylate product and for separation and recycle of isobutane and hydrogen fluoride. The high strength catalyst phase formed in settler 20 is removed via conduit 22 at the rate of 4,050 barrels per day. Valves 24 and 26 are adjusted so that a first portion of the hydrogen fluoride stream in conduit 22 is passed into conduit 23 at the rate of 2,925 barrels per day and a second portion is passed into conduit 25 at the rate of 1,125 barrels per day. The high strength catalyst in conduit 25 is passed into conduit 11 in order to replace hydrogen fluoride lost from the lower strength catalyst phase employed in reactor 5. Substantially pure hydrogen fluoride is passed into the operation via conduit 15 at the rate of 750 barrels per day. The substantially pure hydrogen fluoride passed into conduit 15 is provided by conventional regeneration of the low strength catalyst removed from the operation via conduit 13 and by conventional recovery of hydrogen fluoride dissolved in the hydrocarbon phase which is passed out of the operation via conduit 21. The high strength catalyst phase in conduit 23 is passed into conduit 15 and the resulting catalyst stream is passed into conduit 17 at the rate of 4,050 barrels per day.

We claim as our invention:

1. A process for producing an alkylation reaction product from an isoparaffin and an olefin, which comprises the steps of:
   a. reacting said olefin with said isoparaffin in admixture with a relatively low strength hydrogen fluoride catalyst containing 75 to 95 wt. percent HF at a catalyst to hydrocarbon volume ratio of 1:1 to 5:1;
   b. settling the resultant reaction mixture of step (a) to separate the same into a hydrocarbon phase and a catalyst phase;
   c. commingling with said hydrocarbon phase, without further addition of olefin, a relatively high strength catalyst of hydrogen fluoride and organic diluent containing 90 to 98 wt. percent HF, and 2 to 10 wt. percent of organic diluent, said catalyst having a higher strength than the catalyst utilized in step (a) and in a lower catalyst to hydrocarbon volume ratio than step (a);
   d. introducing the resulting mixture of step (c) into a soaking zone and therein isomerizing lower octane alkylate hydrocarbons to higher octane alkylate hydrocarbons, converting alkyl fluorides into high quality alkylate and HF acid, by maintaining said mixture in the soaking zone at a temperature of 50° to 120° F for 5 to 20 minutes;
   e. separating the effluent of the soaking zone into a second hydrocarbon phase and a second catalyst phase, and;
   f. recovering said alkylation reaction product from said second hydrocarbon phase.

2. The process of claim 1 wherein at least a portion of said second catalyst phase is supplied to step (a).

3. The process of claim 1 wherein the strength of said second catalyst phase is controlled by admixing substantially pure hydrogen fluoride with said low strength hydrogen fluoride catalyst from step (a).

4. The process of claim 1 wherein the relatively high strength hydrogen fluoride catalyst in step (c) contains about 95 wt. percent HF acid and about 5 wt. percent organic diluent.

5. The process of claim 1 wherein at least a portion of said second catalyst phase is recycled to said soaking zone after separation from said second hydrocarbon phase.

6. The process of claim 1 wherein from about 0.01 to about 1 volume of said second catalyst phase is introduced into said soaking zone for each volume of said first hydrocarbon phase introduced into said soaking zone.

7. The process of claim 1 wherein said low strength catalyst phase contains 80 to 98 wt. percent HF.

8. The process of claim 1 wherein said isoparaffin is isobutane.

9. The process of claim 1 wherein said olefin-acting agent is mono-olefin selected from propylene, butenes and pentenes.

10. The process of claim 1 wherein said olefin-acting agent is an alkyl fluoride selected from propyl fluoride, butyl fluorides and pentyl fluorides.

* * * * *